United States Patent
Ishii et al.

(10) Patent No.: US 8,035,902 B2
(45) Date of Patent: Oct. 11, 2011

(54) OPTICAL UNIT FOR PROBE AND OPTICAL UNIT PRODUCING METHOD

(75) Inventors: Shuichi Ishii, Saitama (JP); Daisuke Ayame, Saitama (JP)

(73) Assignee: Fujifilm Corporation, Tokyo (JP)

( * ) Notice: Subject to any disclaimer, the term of this patent is extended or adjusted under 35 U.S.C. 154(b) by 127 days.

(21) Appl. No.: 12/412,752

(22) Filed: Mar. 27, 2009

(65) Prior Publication Data
US 2009/0244727 A1 Oct. 1, 2009

(30) Foreign Application Priority Data
Mar. 28, 2008 (JP) ................. 2008-085622

(51) Int. Cl.
G02B 7/02 (2006.01)
(52) U.S. Cl. ......................................... 359/811
(58) Field of Classification Search ............ 359/811, 359/819, 820; 600/175, 176
See application file for complete search history.

(56) References Cited

U.S. PATENT DOCUMENTS

| 5,536,244 | A | 7/1996 | Muller et al. |
| 5,894,369 | A | 4/1999 | Akiba et al. |
| 7,471,472 | B2 | 12/2008 | Ayame et al. |
| 2002/0186478 | A1* | 12/2002 | Watanabe et al. ......... 359/819 |
| 2004/0156124 | A1* | 8/2004 | Okada ....................... 359/754 |
| 2007/0253077 | A1 | 11/2007 | Ayame et al. |

FOREIGN PATENT DOCUMENTS

| EP | 1 880 656 A1 | 1/2008 |
| JP | 2000-121961 A | 4/2000 |
| JP | 2004-240346 A | 8/2004 |
| JP | 2007-208533 A | 8/2007 |

* cited by examiner

*Primary Examiner* — Joseph P Martinez
(74) *Attorney, Agent, or Firm* — Birch, Stewart, Kolasch & Birch, LLP.

(57) ABSTRACT

A probe apparatus in combination with an endoscope includes a confocal laser probe for in-vivo imaging. The probe is insertable through a forceps channel of an endoscope, and has an optical unit. There is a lens barrel. Plural lens optics are mounted in the lens barrel. The plural lens optics include first lens optics disposed on an object side, and opposed to an object within a body. An optically inactive surface is formed with the first lens optics, and has at least one portion protruding from a barrel end surface of the lens barrel on the object side. Preferably, a height difference of protruding the optically inactive surface from the barrel end surface is 10-500 microns. The portion of the optically inactive surface protruding from the barrel end surface is coated with adhesive agent, for adhesion of the first lens optics thereto.

18 Claims, 9 Drawing Sheets

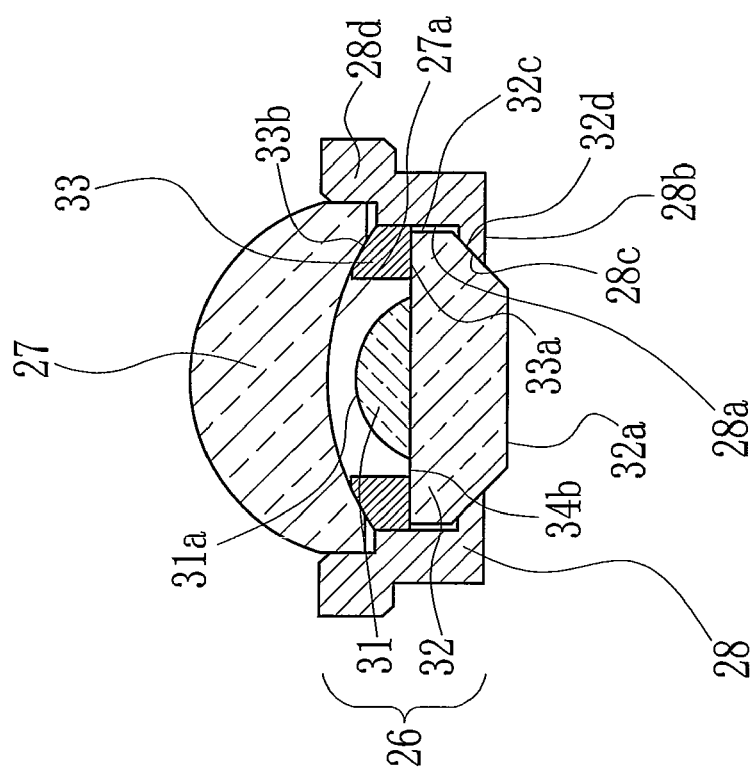
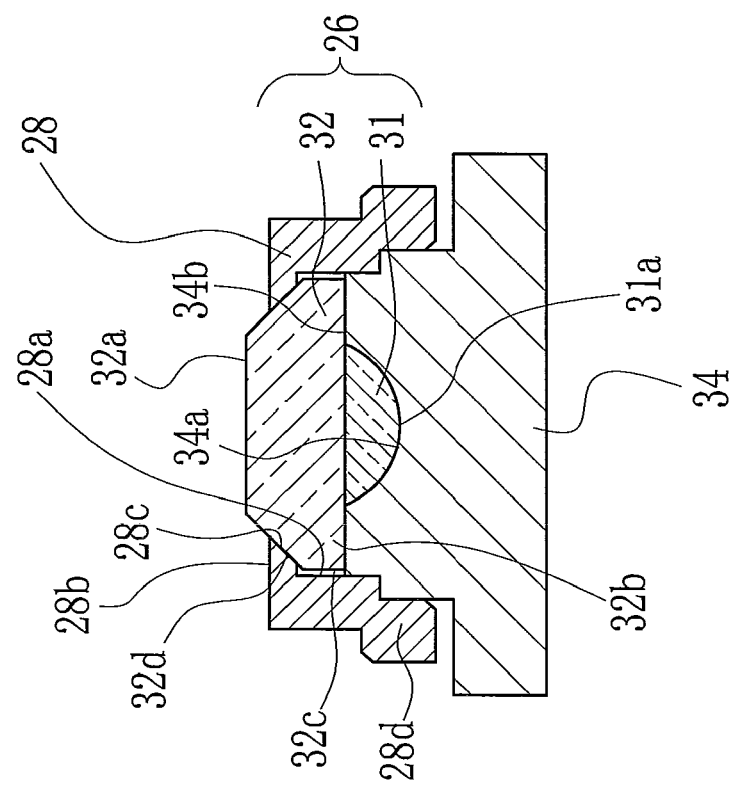

OPTICAL UNIT FOR PROBE AND OPTICAL UNIT PRODUCING METHOD

BACKGROUND OF THE INVENTION

1. Field of the Invention

The present invention relates to an optical unit for a probe, and optical unit producing method. More particularly, the present invention relates to an optical unit for a probe, and optical unit producing method, in which the probe of a probe apparatus is used for in-vivo imaging of a tissue in a human cavity of a patient's body, and an image of the tissue can be stably obtained owing to an improved assembly of the optical unit.

2. Description Related to the Prior Art

A confocal laser probe of a probe apparatus is known, including an optical unit disposed at a distal end of single-mode optical fibers. The optical unit applies laser light to a tissue of a gastrointestinal tract in a patient Is body. Among components of the laser light reflected by the tissue, only reflected light at the focal plane of the optical unit on an object side, an object image of the tissue is obtained. U.S. Pat. Pub. No. 2004/156124 (corresponding to JP-A 2004-240346) discloses an example of the confocal laser probe. According to optical tomography, a two-dimensional image can be obtained at a depth of approximately 100 microns under the surface of mucous membranes by scanning the tissue with the laser light.

JP-A 2000-121961 discloses the use of the confocal laser probe by insertion in a forceps channel of an electronic endoscope. The confocal laser probe must have a small outer diameter for the purpose of reducing physical load to a patient Is body. Also, it is necessary for the optical unit to have a high numerical aperture NA, because a focal plane of the optical unit should be set for a position with a depth from a surface of the tissue. A high value of the numerical aperture NA is essentially necessary specifically with a great wavelength of the laser light in order to create images of high definition.

Lens optics constituting the optical unit must have very fine sizes owing to technical progress according to small diameters and high value of the numerical aperture NA. It has been very difficult to position the lens optics with one another at very high precision. U.S. Pat. No. 7,471,472 (corresponding to JP-A 2007-208533) discloses a method of assembling the lens optics by use of a specialized tool in order to determine intervals between the lens optics precisely.

Owing to requirement of fine sizes of the lens optics in the optical unit, a distance between the focal plane and a first lens/lens group opposed to the tissue is made as small as 50 microns. It is necessary for the first lens/lens group to contact the tissue. An image in the tissue cannot be created with high quality if the contact between the first lens/lens group and the tissue is insufficient.

A portion of the first lens/lens group at the distal end of the lens barrel is coated with adhesive agent for reinforcement. However, various problems arise with the structure of the end of the first lens/lens group flush with the distal end of the lens barrel, for example, difficulty in applying a coating, insufficiency in the reinforcement, addition of a step of wiping the adhesive agent to remove dirt of the first lens/lens group, and the like.

SUMMARY OF THE INVENTION

In view of the foregoing problems, an object of the present invention is to provide an optical unit for a probe, and optical unit producing method, in which the probe of a probe apparatus is used for in-vivo imaging of a tissue in a human cavity of a patient's body, and an image of the tissue can be stably obtained owing to an improved assembly of the optical unit.

In order to achieve the above and other objects and advantages of this invention, an optical unit for a probe insertable through a forceps channel of an endoscope for use is provided. There is a lens barrel. Plural optics are mounted in the lens barrel. The plural optics include first optics disposed on an object side, and opposed to an object within a body. An optically inactive surface is formed with the first optics, having at least one portion protruding from a barrel end surface of the lens barrel on the object side.

The probe is a confocal laser probe.

An amount of protruding the optically inactive surface from the barrel end surface is equal to or more than 10 microns and equal to or less than 500 microns.

In a preferred embodiment, an amount of protruding the optically inactive surface from the barrel end surface is equal to or more than 20 microns and equal to or less than 250 microns.

The optically inactive surface is disposed on a peripheral edge of the first optics.

The portion of the optically inactive surface protruding from the barrel end surface is coated with adhesive agent, for adhesion of the first optics thereto.

The adhesive agent constitutes a layer for preventing entry of light to the portion of the optically inactive surface protruding from the barrel end surface.

The first optics have a plane surface or convex surface directed on the object side.

The first optics are lens optics having a curved surface on a side opposite to the object side.

The first optics include a hemispherical lens element. A plate element is disposed on the object side, and having a diameter greater than the hemispherical lens element.

The first optics are a single lens element.

In a preferred embodiment, the first optics are a glass cover having plane surfaces on the object side and on a side opposite thereto.

The plural optics are plural lens optics. Furthermore, a lens holder is secured inside the lens barrel, for retaining the plural lens optics. The lens holder has a holder end surface flush with the barrel end surface.

Furthermore, a spacer ring is disposed between the plural lens optics, for setting the plural lens optics at a predetermined interval.

The probe constitutes a component of a probe apparatus. The probe apparatus transmits illumination light to the probe with optical fiber, receives object light from the object with the probe, transmits the object light with the optical fiber, and detects the object light.

In one aspect of the invention, an optical unit producing method of producing an optical unit for a probe insertable through a forceps channel of an endoscope for use is provided. The optical unit includes a lens barrel, plural optics mounted in the lens barrel, the plural optics including first optics disposed on an object side, and opposed to an object within a body. In the optical unit producing method, at least one portion of an optically inactive surface formed with the first optics is protruded from a barrel end surface of the lens barrel on the object side. The portion of the optically inactive surface protruding from the barrel end surface is coated with adhesive agent, for adhesion of the first optics thereto.

Accordingly, an image of tissue can be stably obtained owing to an improved assembly of the optical unit, because the probe can access the tissue with high closeness easily.

BRIEF DESCRIPTION OF THE DRAWINGS

The above objects and advantages of the present invention will become more apparent from the following detailed description when read in connection with the accompanying drawings, in which:

FIGS. 6A and 6B are horizontal sections illustrating a step of assembling second lens optics on the first lens optics and the lens holder;

DETAILED DESCRIPTION OF THE PREFERRED EMBODIMENT(S) OF THE PRESENT INVENTION

Figure 1:
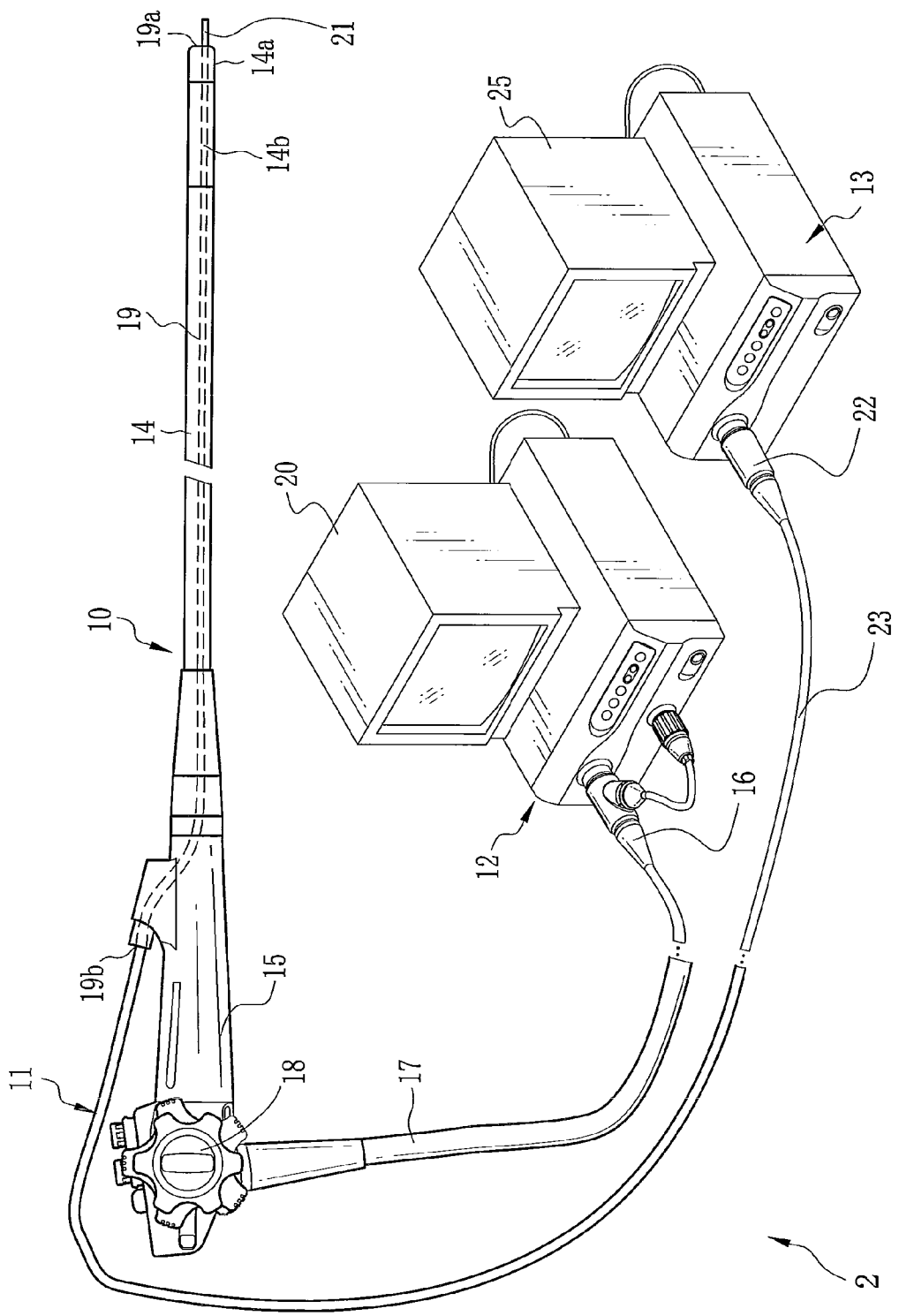
FIG. 1 is an explanatory view illustrating an endoscope system and a probe apparatus.

In FIG. 1, an endoscope system 2 includes an electronic endoscope 10 and a processor 12 in connection with the endoscope 10 for endoscopic imaging. Also, a probe apparatus is associated with the endoscope system 2, and includes a confocal laser probe 11 and a control processor 13. A forceps channel 19 is formed through the endoscope 10. The confocal laser probe 11 is inserted through the forceps channel 19 for use. The control processor 13 is connected with the confocal laser probe 11 for confocal laser imaging and observation. The endoscope 10 includes an insertion tube 14, a handle 15, a connector 16 and a universal cable 17. The insertion tube 14 is flexible and enters a human cavity or gastrointestinal tract of a patient's body. The handle 15 is disposed at a proximal end of the insertion tube 14. The connector 16 is connectable with the processor 12. The universal cable 17 extends between the handle 15 and the connector 16 for connection.

A head assembly 14a is disposed at a distal end of the insertion tube 14 and contains a CCD (not shown) for imaging in the body. In the insertion tube 14, a steering portion 14b is disposed at a proximal end of the head assembly 14a, and constituted by plural steering segments. When a steering wheel 18 on the handle 15 is rotated manually, wire through the insertion tube 14 is moved back and forth for bending the steering portion 14b up and down and to the right and left. Thus, the head assembly 14a is bent in a desired direction in the body.

The forceps channel 19 extends through the insertion tube 14. A first forceps opening 19a of the forceps channel 19 is open in the head assembly 14a. A second forceps opening 19b of the forceps channel 19 is open in the handle 15.

The processor 12 includes a light source of a well-known structure, and signal processing circuit and other circuits. When the light source is turned on with the connector 16 connected to the processor 12, light from the light source enters a light guide (not shown) extending from the connector 16 of the endoscope 10 toward the head assembly 14a. The light is transmitted by the light guide and emitted by a lighting window (not shown) in the head assembly 14a toward an object in the body. The light is reflected by the object and is picked up by the CCD inside the head assembly 14a. An image signal is output by the CCD, and transmitted to the processor 12. A monitor display panel 20 is caused by the processor 12 to display an image according to image data into which the image signal is converted by the processor 12. A motion image or live image, or still image is displayed on the display panel 20.

The confocal laser probe 11 in the probe apparatus includes a confocal optical unit 21 or lens assembly, a connector 22 and a cable 23. The confocal optical unit 21 has an optical system for forming an image of an object. The connector 22 is disposed at a proximal end, and connectable with the control processor 13. The cable 23 extends between the confocal optical unit 21 and the connector 22 for connection. A fiber bundle 24 extends through the cable 23 and is constituted by a plurality of single-mode optical fibers for light transmission. See FIG. 2. The confocal laser probe 11 is inserted in the second forceps opening 19b of the endoscope 10 and through the forceps channel 19, so that a distal end of the confocal optical unit 21 protrudes from the first forceps opening 19a of the head assembly 14a. An image of an object in the body can be obtained by the confocal laser probe 11. For imaging, a distal end of the confocal optical unit 21 is set in contact with a surface of the tissue of the object, including an object side surface 32a of first lens optics 26, a holder end surface 28b of a lens holder or frame 28, and a barrel end surface 29b of a lens barrel 29. See FIG. 3.

The control processor 13 includes a laser light source of a well-known structure, and signal processing circuit and other circuits. When the laser light source is turned on with the connector 22 of the confocal laser probe 11 connected to the control processor 13, laser light from the laser light source enters the fiber bundle 24, and travels toward the confocal optical unit 21. The laser light from the single-mode optical fibers enters a confocal optical system 30 or lens system in the confocal optical unit 21 in the probe apparatus. See FIG. 2. The laser light is focused by the confocal optical system 30 on the object of interest. The light is reflected by the object and travels back in the single-mode optical fibers through the confocal optical system 30.

A distal end of the single-mode optical fibers has a very small core or opening, which operates as a point light source and an aperture. The inside of the single-mode optical fibers receives entry of only incident light reflected from a position conjugate with the end on the object side of the single-mode optical fibers or the focused point of the laser light in the object among components of the reflected light from the object. The incident light is transmitted by the single-mode optical fibers, and input to the control processor 13. The control processor 13 receives a point image of incident light obtained as image light by scanning an object of interest with laser light, and processes a signal obtained by conversion of the point image. A display panel 25 is caused by the control processor 13 to display a confocal scan image or observation image at a high magnification and high resolution.

Figure 2:
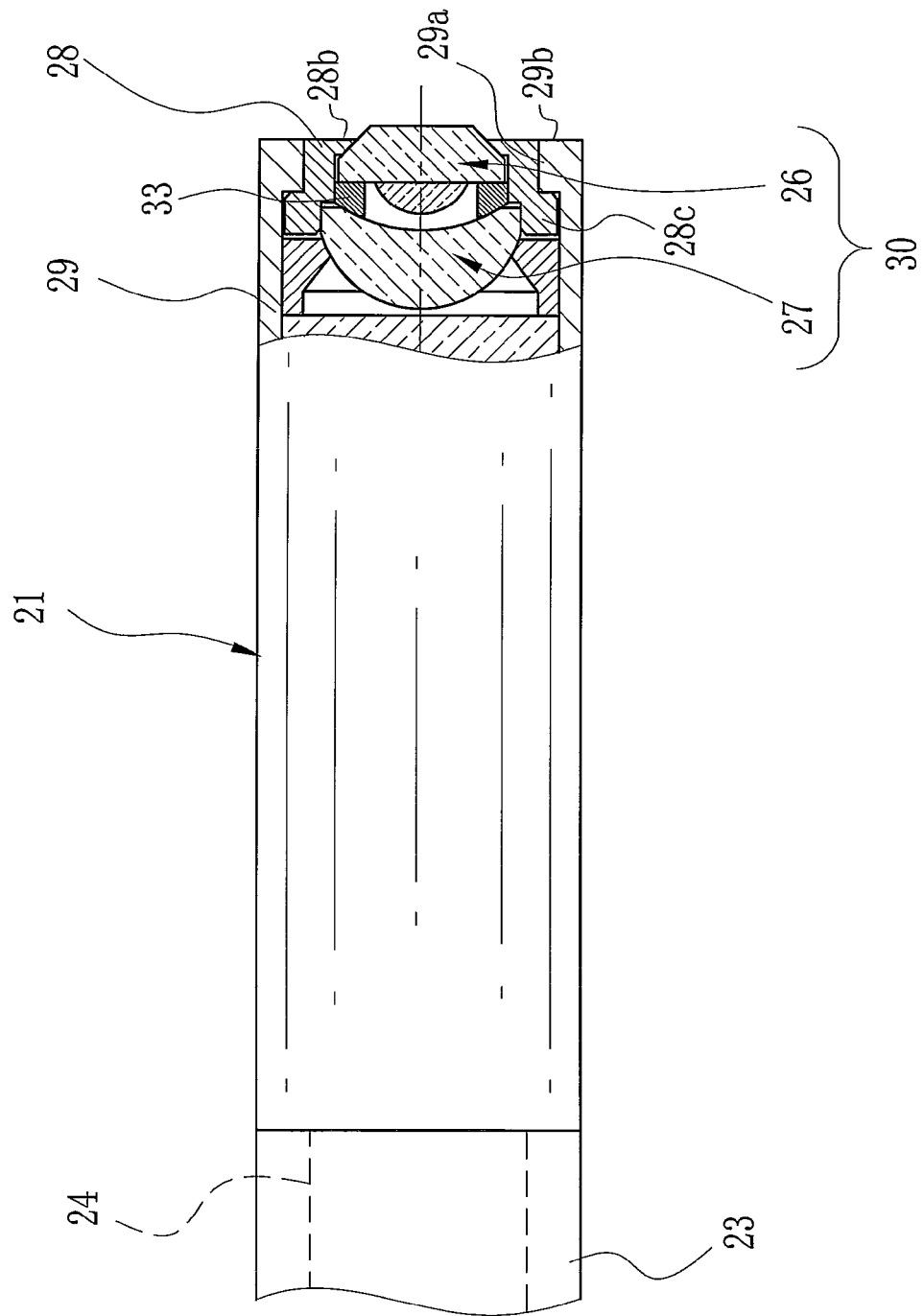
FIG. 2 is a horizontal section partially cutaway, illustrating a confocal laser probe of the probe apparatus.
Figure 3:
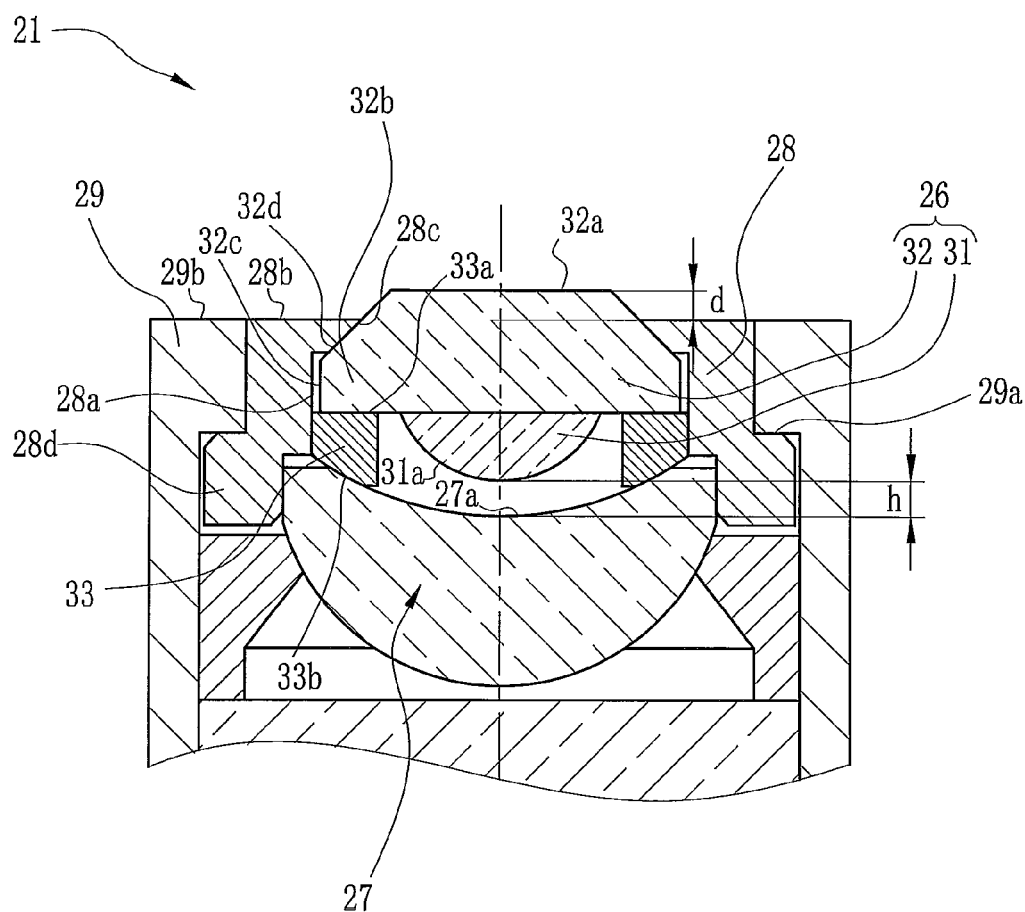
FIG. 3 is a horizontal section illustrating the confocal laser probe with first lens optics.

In FIGS. 2 and 3, the confocal optical unit 21 includes the first lens optics 26, second lens optics 27, the lens holder 28 and the lens barrel 29. The first lens optics 26 are directed to an object of interest to be imaged. The second lens optics 27 are opposed to a lens surface 31a of the first lens optics 26 opposite to the object side. The lens holder 28 retains the first and second lens optics 26 and 27 mounted thereon. The lens barrel 29 supports the lens holder 28. The confocal optical unit 21 includes the confocal optical system 30, which is constituted by the first and second lens optics 26 and 27 among a plurality of lens optics (not shown). All of the plural lens optics in the confocal optical system 30 are contained in the lens barrel 29, including the first and second lens optics 26 and 27.

Figure 4:
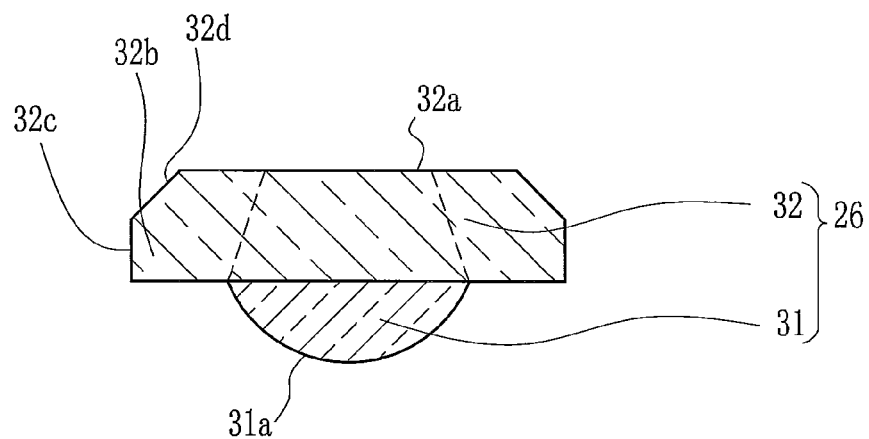
FIG. 4 is a horizontal section illustrating the first lens optics.

In FIG. 4, the first lens optics 26 include a hemispherical lens element 31 and a plate element 32 which is disposed on an object side and has a greater diameter than the hemispherical lens element 31. The plate element 32 as an originally separate element is attached to the hemispherical lens element 31. In the first lens optics 26, the object side surface 32a of the plate element 32 is directed opposite to the lens surface 31a of the hemispherical lens element 31. A flange portion 32b is a peripheral portion of the plate element 32 and protrudes from the hemispherical lens element 31. The flange portion 32b has a ring shape to extend circularly. Note that a flange portion may protrude only partially from the peripheral edge of the hemispherical lens element 31. A peripheral surface 32c of the flange portion 32b has a diameter slightly smaller than that of an inner surface 28a of the lens holder 28.

An outer diameter of the hemispherical lens element 31 is an effective diameter as the entirety of the hemispherical lens element 31 operates optically. In the drawing, the broken line in the plate element 32 indicates its optically active portion, which is in a shape of a frustum of a cone extending from an interface on the hemispherical lens element 31 toward the object side surface 32a. The flange portion 32b is an optically inactive portion disposed beside a central portion of the plate element 32 as optically active portion.

An inclined surface 32d is formed with the flange portion 32b and extends conically from the peripheral surface 32c toward the object side surface 32a. The inclined surface 32d is an optically inactive surface in portions of the first lens optics 26, and used for positioning relative to the lens holder 28.

In FIG. 3, the lens holder 28 is shaped cylindrically. An inclined surface 28c is formed conically with a decreasing diameter toward the holder end surface 28b on the object side. A minimum diameter of the inclined surface 28c is greater than a minimum diameter of the inclined surface 32d of the flange portion 32b. When the peripheral surface 32c of the flange portion 32b is fitted on the inner surface 28a of the lens holder 28 to set the inclined surface 28c of the lens holder 28 tightly on the inclined surface 32d of the flange portion 32b, then a portion of the inclined surface 32d of the first lens optics 26 and the object side surface 32a protrude from the holder end surface 28b by a height difference d. The barrel end surface 29b is flush with the holder end surface 28b. Thus, the first lens optics 26 are positioned on the lens holder 28. Note that the positioning surface for positioning the first lens optics 26 on the lens holder 28 is not limited to the inclined surface 32d, but may be formed on the flange portion 32b in a form concentric with an edge of the object side surface 32a on the object side and with a stepped portion.

A ring-shaped ridge 28d protrudes from the lens holder 28 at the end and on a probe side opposite to the object side, and is shaped in a step form which extends in parallel to the object side surface 32a. A retention portion 29a is formed at an end of the lens barrel 29, and retains the ring-shaped ridge 28d. The holder end surface 28b is kept flush with the barrel end surface 29b when retained by the retention portion 29a. Note that the ring-shaped ridge 28d may have a shape other than the step form, for example an inclined surface oriented to the object side.

A spacer ring 33 is disposed on the flange portion 32b opposite to the object side surface 32a of the plate element 32, and regulates a distance between the lens surface 31a and a concave surface 27a of the second lens optics 27 at an interval h. The spacer ring 33 includes a plane surface 33a and a curved surface 33b. The plane surface 33a contacts the first lens optics 26 at the flange portion 32b, and is parallel with the object side surface 32a. The curved surface 33b contacts an edge of the concave surface 27a. The spacer ring 33 is sandwiched by the first and second lens optics 26 and 27 by contact of the plane surface 33a and the curved surface 33b. As the flange portion 32b is formed with the first lens optics 26, an area of contact with the spacer ring 33 is sufficiently large. Thus, the second lens optics 27 can be positioned with the first lens optics 26 at a high precision.

An assembling method for the confocal optical unit 21 is illustrated in FIGS. 5A-8B. At first, the first lens optics 26 are coated with an anti-reflection layer before the step of FIGS. 5A and 5B in order to derive dim reflected light from the tissue of the body efficiently. In the step of applying the coating, the flange portion 32b is held for supporting the first lens optics 26.

Figure 5A:
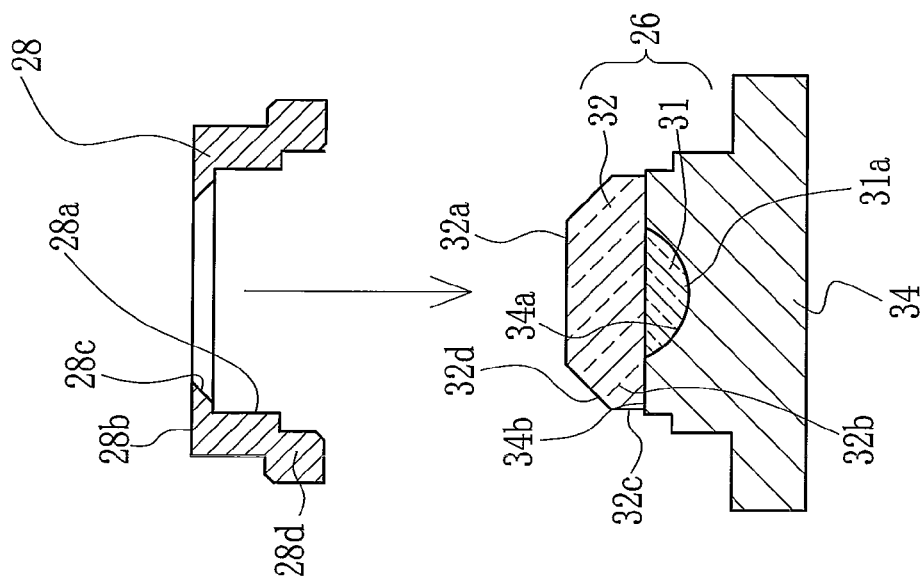
FIGS. 5A and 5B are explanatory views in horizontal sections illustrating a step of assembling the first lens optics on a lens holder.
Figure 5B:
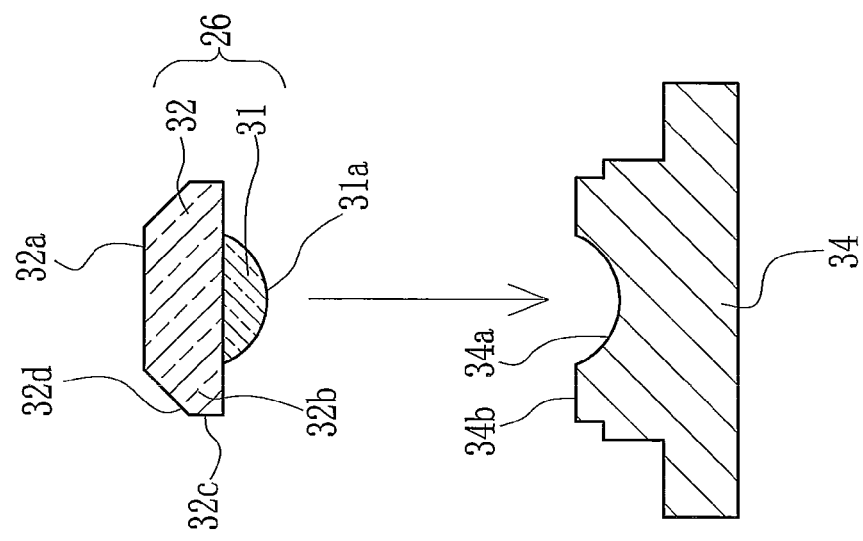

Then a step of setting the first lens optics 26, the spacer ring 33 and the second lens optics 27 on the lens holder 28 is described by referring to FIGS. 5A and 5B. At first, the lens surface 31a of the first lens optics 26 opposite to the object side is set in firm contact with a first receiving surface 34a of a support tool 34. The flange portion 32b is set in firm contact with a second receiving surface 34b formed around the first receiving surface 34a.

Then the lens holder 28 is set firmly on the first lens optics 26 supported by the support tool 34. See FIGS. 5B and 6A. The peripheral surface 32c of the first lens optics 26 is fitted in the inner surface 28a of the lens holder 28. The inclined surface 32d of the first lens optics 26 is tightly set on the inclined surface 28c of the lens holder 28, so that the first lens optics 26 are positioned suitably on the lens holder 28. As has been described heretofore, the inclined surface 32d of the first lens optics 26 and the object side surface 32a protrude from the holder end surface 28b. Thus, the first lens optics 26 are retained on the lens holder 28.

Figure 7:
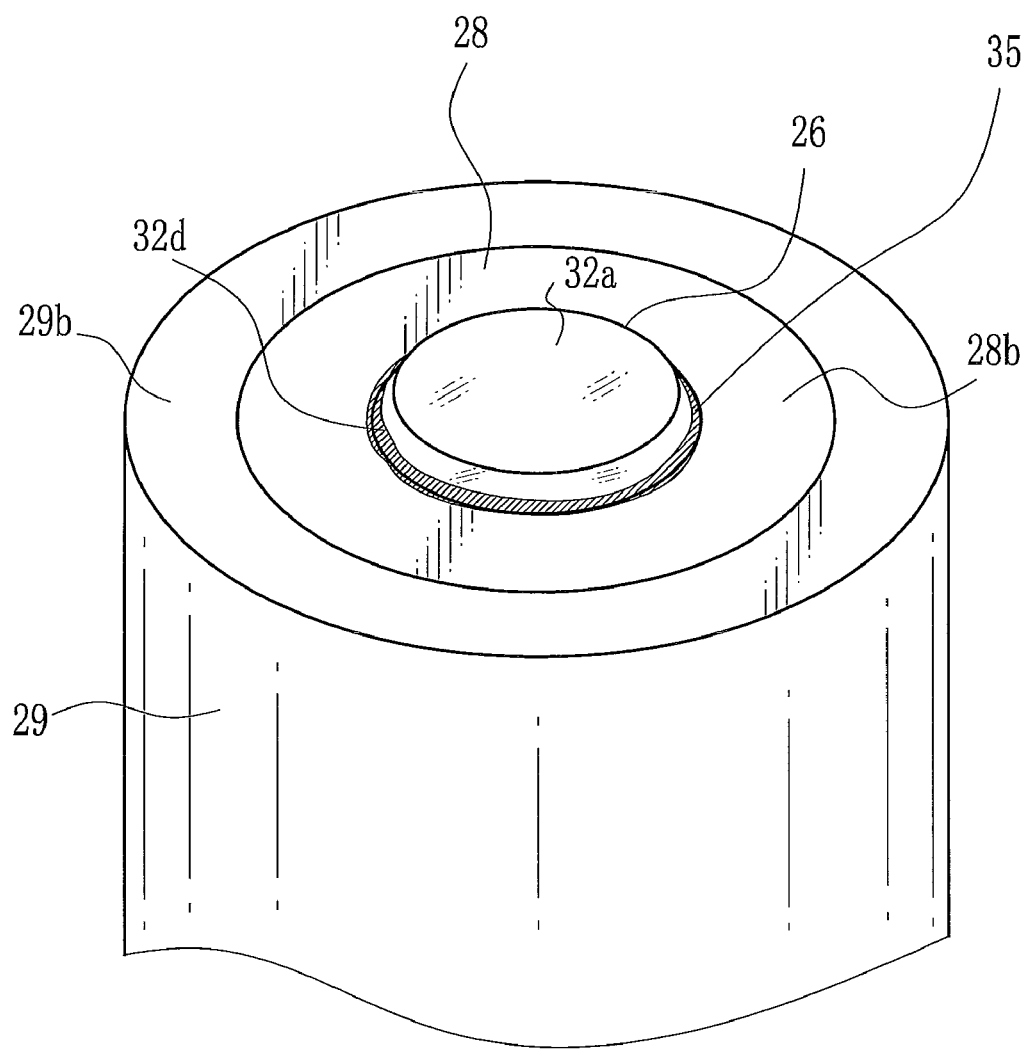
FIG. 7 is a perspective view illustrating the confocal lens probe with an area of applying adhesive agent.

To fit the first lens optics 26 on the lens holder 28, the inner surface 28a is attached to the peripheral surface 32c of the flange portion 32b. Furthermore, adhesive agent is applied to portions other than this portion for tightly securing the first lens optics 26 to the lens holder 28. In FIG. 7, the use of adhesive agent 35 is illustrated. The barrel end surface 29b of the lens barrel 29 and a large diameter area of the inclined surface 32d of the first lens optics 26 projecting from the barrel end surface 29b are coated with the adhesive agent 35. As the inclined surface 32d operates as a space for the adhesive agent 35, the adhesive agent 35 will not stick on the object side surface 32a. The lens holder 28 can be attached to the first lens optics 26 in a good condition. Note that the adhesive agent 35 for the inclined surface 32d protruding from the barrel end surface 29b contains a light shielding material such as carbon black or the like, and operates as light shielding layer for preventing entry of light through the inclined surface 32d into the first lens optics 26.

Let d be a height difference with which the inclined surface 32d of the first lens optics 26 protrudes from the barrel end surface 29b when the first lens optics 26 are retained on the lens holder 28 in FIG. 3. The height difference d is equal to or more than 10 microns and equal to or less than 500 microns, and preferably equal to or more than 20 microns and equal to or less than 250 microns.

Should the height difference d be smaller than 10 microns, the adhesive agent 35 will overflow to the object side surface 32a due to an insufficient space for the adhesive agent 35. Should the height difference d be greater than 500 microns, there occurs a space between the barrel end surface 29b and the tissue surface of the body because a thickness of mucus on the tissue surface is approximately 500 microns. When the object side surface 32a contacts the tissue surface, it is likely that no good image can be created. The preferable lower limit of 20 microns for the height difference d is for the purpose of keeping a sufficient space of the adhesive agent 35 in good working efficiency in applying a coating of the adhesive agent 35. The preferable upper limit of 250 microns for the height difference d is for the purpose of reliably creating a good image without clearance between the barrel end surface 29b and the tissue surface.

In FIGS. 6A and 6B, the support tool 34 is removed from the first lens optics 26 and the lens holder 28 after attachment between those. Then the plane surface 33a of the spacer ring 33 is set in tight contact with the flange portion 32b of the first lens optics 26. The curved surface 33b of the spacer ring 33 is set in tight contact with an edge of the concave surface 27a of the second lens optics 27 on the object side. See FIG. 6B.

Accordingly, the distance between the first and second lens optics 26 and 27 can be the interval h as illustrated in FIG. 3. The second lens optics 27 are retained on the lens holder 28 with the interval h. Specifically, the second lens optics 27 are attached to the lens holder 28 by adhesion. Therefore, the first and second lens optics 26 and 27, the spacer ring 33 and the lens holder 28 are combined as one component.

Figure 8A:
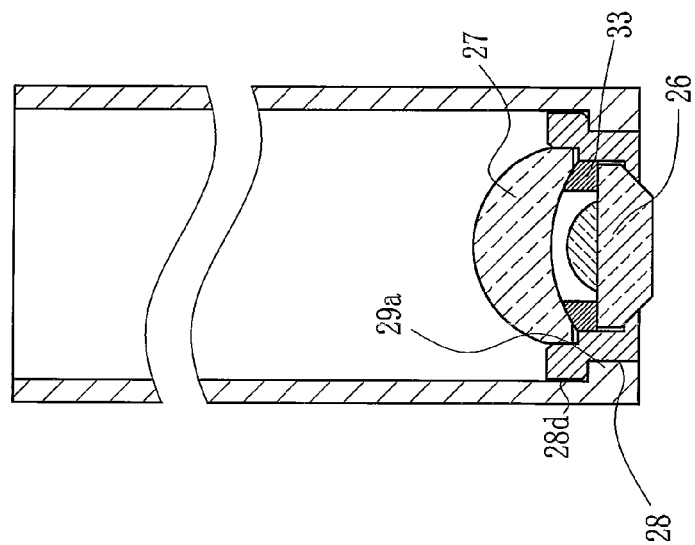
FIGS. 8A and 8B are horizontal sections illustrating a step of assembling a confocal optical unit.
Figure 8B:
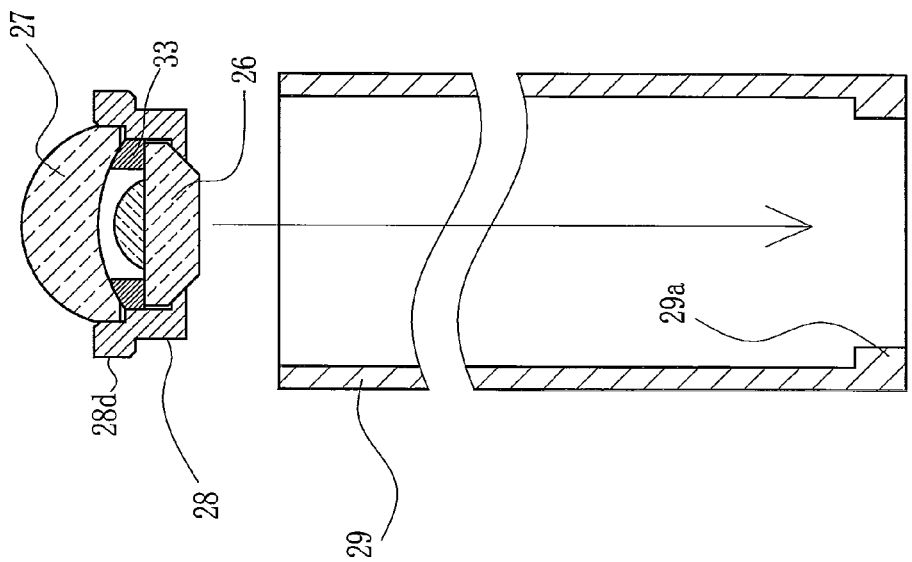

In FIGS. 8A and 8B, a step of attaching the first and second lens optics 26 and 27, the spacer ring 33 and the lens holder 28 to an end of the lens barrel 29 is illustrated. At first, the lens holder 28 is inserted through a space on a probe side opposite to the object side in the lens barrel 29. See FIG. 8A. The ring-shaped ridge 28d of the lens holder 28 is retained on the retention portion 29a formed at the end of the lens barrel 29. See FIG. 8B. Thus, the lens holder 28 is fitted firmly in the lens barrel 29. One portion of the inclined surface 32d projects toward the object side as optically inactive surface of the first lens optics 26 from the barrel end surface 29b. The barrel end surface 29b is flush with the holder end surface 28b in combination of the lens holder 28 with the lens barrel 29. See FIGS. 2 and 3. After attachment of the lens holder 28 to the lens barrel 29, other lens elements are assembled together to obtain the confocal optical unit 21.

Thus, the plate element 32 as optically inactive surface of the first lens optics 26 is kept protruded from the barrel end surface 29b toward the object side. The object side surface 32a of the first lens optics 26 is easy to access and contact the tissue in the body so as to obtain an image stably from the tissue in the confocal laser probe 11.

The adhesive agent 35 is applied to a large diameter area of the inclined surface 32d protruding from the holder end surface 28b, to attach the first lens optics 26 to the lens holder 28. Thus, the reliability in the adhesion can be high as the application of the adhesive agent 35 is facilitated. The object side surface 32a of the first lens optics 26 does not pollute with dirt, so that no wiping of the adhesive agent 35 is necessary. It is possible to obtain high reliability of the confocal optical unit 21 as product, and raise working efficiency in producing the confocal optical unit 21. It is unnecessary to form an additional layer for shielding light, as the adhesive agent 35 operates as layer for shielding light.

Figure 9:
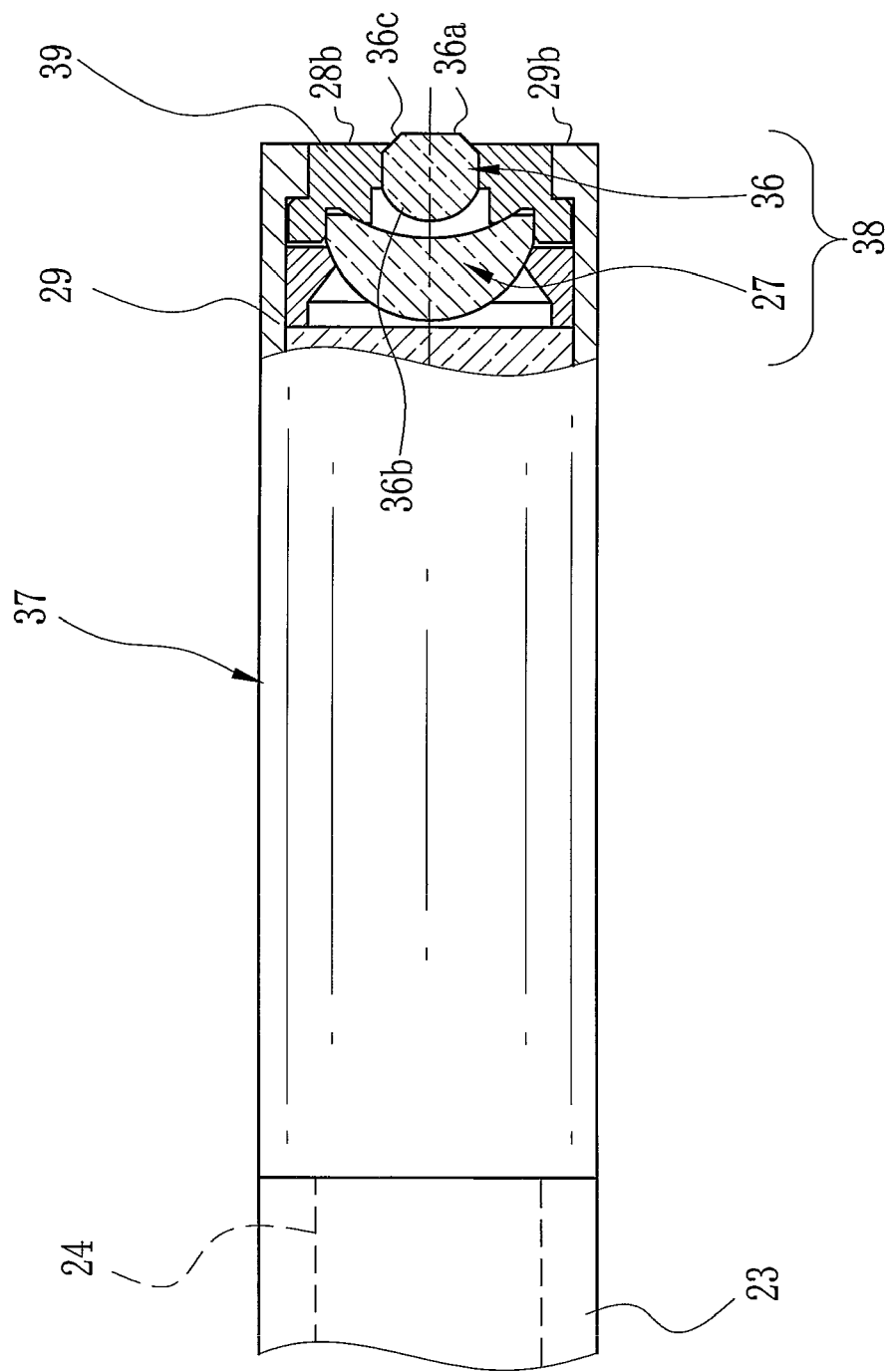
FIG. 9 is a horizontal section partially cutaway, illustrating one preferred confocal optical unit having a single lens element as first lens optics.

In FIG. 9, one preferred embodiment is illustrated, in which first lens optics 36 have no flange portion. An object side surface 36a of the first lens optics 36 is plane. A lens surface 36b of the first lens optics 36 is spherical on the probe side opposite to the object side. A confocal optical unit 37 or lens assembly in the probe apparatus includes a confocal optical system 38 or lens system, and a lens holder or frame 39. The confocal optical system 38 includes the first lens optics 36 and the second lens optics 27. The lens holder 39 has a portion of a spacer ring as one piece.

An inclined surface 36c is located on the periphery of the object side surface 36a on the object side, protrudes from the barrel end surface 29b of the lens barrel 29 as optically inactive surface, and has a shape of a frustum of a cone. In a manner similar to the above embodiment, the adhesive agent 35 is applied to a large diameter area in the inclined surface 36c protruding from the holder end surface 28b of the lens holder 28. Note that the shape of the first lens optics 36 is not limited. For example, the inclined surface 36c may not be formed. A peripheral edge of the object side surface 36a in the first lens optics 36 may be shaped in a smoothly curved form with a gradually increasing diameter instead of the conical shape. Any shape of protrusion from the barrel end surface 29b may be used as optically inactive surface.

Figure 10:
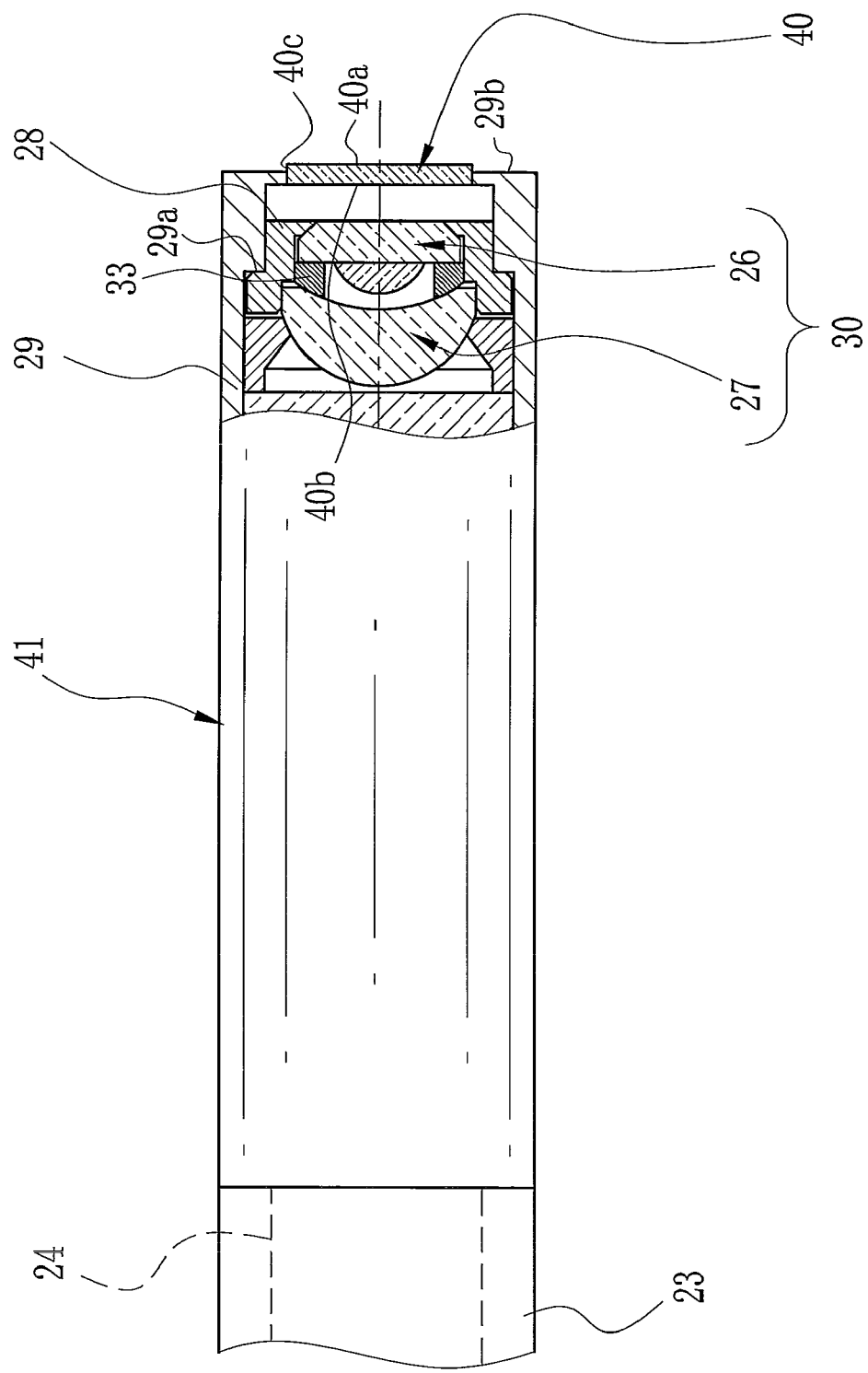
FIG. 10 is a horizontal section partially cutaway, illustrating another preferred confocal optical unit having a glass cover.

In FIG. 10, another preferred embodiment is illustrated, in which a glass cover 40 is first optics in a confocal optical unit 41 of the invention, and covers the first lens optics 26 on the object side. For the confocal optical unit 41 or lens assembly in the probe apparatus, the confocal optical unit 21 of FIG. 2 is repeated but with a difference in having the glass cover 40.

A first glass surface 40a of the glass cover 40 is on the object side. A second glass surface 40b of the glass cover 40 is opposite to the first glass surface 40a. Both of the glass surfaces 40a and 40b are plane, and are optically inactive. Also, a surface of a peripheral edge 40c around the first glass surface 40a is optically inactive. At least one portion of the peripheral edge 40c protrudes from the barrel end surface 29b.

In the above embodiment, the object side surface 32a of the first lens optics 26 or 36 is plane. However, an object side surface of the first lens optics 26 or 36 can be convex.

In the above embodiment, the control processor and the light source device are combined as a single component. However, a light source device may be separate from a control processor. In the above embodiment, the probe apparatus of the invention is associated with the endoscope 10. However, a probe apparatus may be used in connection with an ultrasonic endoscope having an ultrasonic transducer at a distal end, a fiberscope including an optical image guide for imaging an object in a body as endoscope, and the like. Although the probe apparatus of the invention is used for optical tomography for imaging tissues tomographically, a probe apparatus can image a surface of tissues. A probe according to the invention may be a structure other than a confocal laser probe.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An optical unit for a probe insertable through a forceps channel of an endoscope for use, comprising:
   a lens barrel;
   plural optics mounted in said lens barrel;

a lens holder, secured inside said lens barrel, for retaining said plural optics; said plural optics including first optics disposed on an object side, and opposed to an object within a body;

an optically inactive surface, formed with said first optics, having at least one portion protruding from a barrel end surface of said lens barrel on said object side, wherein said optically inactive surface and a first inclined surface are disposed on a peripheral edge of said first optics, and wherein said first inclined surface of said first optics contacts to said lens holder.

2. The optical unit as defined in claim 1, wherein said probe is a confocal laser probe.

3. The optical unit as defined in claim 1, wherein an amount of protruding said optically inactive surface from said barrel end surface is equal to or more than 10 microns and equal to or less than 500 microns.

4. The optical unit as defined in claim 1, wherein an amount of protruding said optically inactive surface from said barrel end surface is equal to or more than 20 microns and equal to or less than 250 microns.

5. The optical unit as defined in claim 1, wherein said portion of said optically inactive surface protruding from said barrel end surface is coated with adhesive agent, for adhesion of said first optics thereto.

6. The optical unit as defined in claim 5, wherein said adhesive agent constitutes a layer for preventing entry of light to said portion of said optically inactive surface protruding from said barrel end surface.

7. The optical unit as defined in claim 1, wherein said first optics have a plane surface or convex surface directed on said object side.

8. The optical unit as defined in claim 1, wherein said first optics are lens optics having a curved surface on a side opposite to said object side.

9. The optical unit as defined in claim 8, wherein said first optics include:

a hemispherical lens element; and a plate element disposed on said object side, and having a diameter greater than said hemispherical lens element.

10. The optical unit as defined in claim 8, wherein said first optics are a single lens element.

11. The optical unit as defined in claim 1, wherein said first optics are a glass cover having plane surfaces on said object side and on a side opposite thereto.

12. The optical unit as defined in claim 1, wherein said plural optics are plural lens optics;

said lens holder has a holder end surface flush with said barrel end surface.

13. The optical unit as defined in claim 12, further comprising a spacer ring, disposed between said plural lens optics, for setting said plural lens optics at a predetermined interval.

14. The optical unit as defined in claim 12, wherein said lens holder includes a second inclined surface formed conically with a decreasing diameter toward said holder end surface, and said first inclined surface is fitted on said second inclined surface.

15. The optical unit as defined in claim 14, wherein a minimum diameter of said second inclined surface is greater than that of said first inclined surface.

16. The optical unit as defined in claim 1, wherein said probe constitutes a component of a probe apparatus;

said probe apparatus transmits illumination light to said probe with optical fiber, receives object light from said object with said probe, transmits said object light with said optical fiber, and detects said object light.

17. An optical unit producing method of producing an optical unit for a probe insertable through a forceps channel of an endoscope for use, said optical unit including a lens barrel, plural optics mounted in said lens barrel, a lens holder, secured inside said lens barrel, for retaining said plural optics; said plural optics including first optics disposed on an object side, and opposed to an object within a body, said optical unit producing method comprising steps of:

protruding at least one portion of an optically inactive surface formed with said first optics from a barrel end surface of said lens barrel on said object side;

coating said portion of said optically inactive surface protruding from said barrel end surface with adhesive agent, for adhesion of said first optics thereto;

disposing said optically inactive surface and a first inclined surface on a peripheral edge of said first optics; and contacting said first inclined surface of said first optics to said lens holder.

18. The optical unit producing method as defined in claim 17, wherein said probe is a confocal laser probe.

* * * * *